US012372547B1

(12) United States Patent
Berme et al.

(10) Patent No.: US 12,372,547 B1
(45) Date of Patent: Jul. 29, 2025

(54) FORCE AND/OR MOTION MEASUREMENT SYSTEM THAT INCLUDES AT LEAST ONE KINEMATIC SENSOR DEVICE AND AT LEAST ONE DATA PROCESSING DEVICE CONFIGURED TO EXECUTE COMPUTER EXECUTABLE INSTRUCTIONS FOR DETERMINING A POSITION AND/OR MOVEMENT OF A PERSON BASED UPON OUTPUT DATA FROM THE AT LEAST ONE KINEMATIC SENSOR DEVICE

(71) Applicant: Bertec Corporation, Columbus, OH (US)

(72) Inventors: Necip Berme, Worthington, OH (US); Murat Kerim Berme, Venice, CA (US); Kuba Sunderland-Ober, Columbus, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 18/222,939

(22) Filed: Jul. 17, 2023

Related U.S. Application Data (63) Continuation-in-part of application No. 17/509,838, filed on Oct. 25, 2021, now Pat. No. 11,705,244.

(51) Int. Cl.
*G01P 13/02* (2006.01)
*G01L 1/00* (2006.01)
*G01S 7/48* (2006.01)
*G01S 13/88* (2006.01)
*G01S 15/88* (2006.01)
*G01S 17/88* (2006.01)

(52) U.S. Cl.
CPC .............. *G01P 13/02* (2013.01); *G01L 1/005* (2013.01); *G01S 7/4804* (2013.01); *G01S 13/88* (2013.01); *G01S 15/88* (2013.01); *G01S 17/88* (2013.01)

(58) Field of Classification Search
None
See application file for complete search history.

(56) References Cited

U.S. PATENT DOCUMENTS

| 5,428,769 | A | 6/1995 | Glaser et al. |
|---|---|---|---|
| 6,038,488 | A | 3/2000 | Barnes et al. |
| 6,113,237 | A | 9/2000 | Ober et al. |
| 6,152,564 | A | 11/2000 | Ober et al. |
| 6,295,878 | B1 | 10/2001 | Berme |
| 6,354,155 | B1 | 3/2002 | Berme |
| 6,389,883 | B1 | 5/2002 | Berme et al. |
| 6,936,016 | B2 | 8/2005 | Berme et al. |
| 7,389,144 | B1 | 6/2008 | Osorio et al. |
| 8,181,541 | B2 | 5/2012 | Berme |
| 8,315,822 | B2 | 11/2012 | Berme et al. |
| 8,315,823 | B2 | 11/2012 | Berme et al. |
| D689,388 | S | 9/2013 | Berme |
| D689,389 | S | 9/2013 | Berme |
| 8,543,540 | B1 | 9/2013 | Wilson et al. |
| 8,544,347 | B1 | 10/2013 | Berme |
| 8,643,669 | B1 | 2/2014 | Wilson et al. |
| 8,700,569 | B1 | 4/2014 | Wilson et al. |
| 8,704,855 | B1 | 4/2014 | Berme et al. |
| 8,764,532 | B1 | 7/2014 | Berme |
| 8,847,989 | B1 | 9/2014 | Berme et al. |
| D715,669 | S | 10/2014 | Berme |
| 8,902,249 | B1 | 12/2014 | Wilson et al. |
| 8,915,149 | B1 | 12/2014 | Berme |
| 9,032,817 | B2 | 5/2015 | Berme et al. |
| 9,043,278 | B1 | 5/2015 | Wilson et al. |
| 9,066,667 | B1 | 6/2015 | Berme et al. |
| 9,081,436 | B1 | 7/2015 | Berme et al. |
| 9,168,420 | B1 | 10/2015 | Berme et al. |
| 9,173,596 | B1 | 11/2015 | Berme et al. |
| 9,200,897 | B1 | 12/2015 | Wilson et al. |
| 9,277,857 | B1 | 3/2016 | Berme et al. |
| D755,067 | S | 5/2016 | Berme et al. |
| 9,404,823 | B1 | 8/2016 | Berme et al. |
| 9,414,784 | B1 | 8/2016 | Berme et al. |
| 9,468,370 | B1 | 10/2016 | Shearer |

(Continued)

OTHER PUBLICATIONS

Jovanov, Emil, et al. "A wireless body area network of intelligent motion sensors for computer assisted physical rehabilitation." Journal of NeuroEngineering and rehabilitation 2 (2005): 1-10.*
BalanceCheck Screener—Protocol Guide, Bertec Corporation, Version 1.1.0, last updated Mar. 2012.
BalanceCheck Trainer—Protocol Guide, Bertec Corporation, Version 1.1.0, last updated Mar. 2012.
Bertec Workbook—Program Documentation, Bertec Corporation, Version 1.1.0, last updated Mar. 2012.
Digital Acquire 4—Program Documentation, Bertec Corporation, Version 4.0.11, last updated Jul. 2012.

(Continued)

*Primary Examiner* — G. Steven Vanni
(74) *Attorney, Agent, or Firm* — The Law Office of Patrick F. O'Reilly III, LLC (57) ABSTRACT

A force and/or motion measurement system is disclosed herein. In one or more embodiments, the force and/or motion measurement system includes at least one kinematic sensor device configured to detect a position and/or movement of a body portion of a person, the at least one kinematic sensor device being mounted in a floor of a room or in a force measurement assembly; and at least one data processing device operatively coupled to the at least one kinematic sensor device, the at least one data processing device including at least one hardware component storing computer executable instructions, and the at least one data processing device configured to execute the computer executable instructions. The computer executable instructions comprise instructions for determining a position and/or movement of the person based upon output data from the at least one kinematic sensor device.

16 Claims, 4 Drawing Sheets

(56) References Cited

U.S. PATENT DOCUMENTS

| | | |
|---|---|---|
| 9,517,008 B1 | 12/2016 | Berme et al. |
| 9,526,443 B1 | 12/2016 | Berme et al. |
| 9,526,451 B1 | 12/2016 | Berme |
| 9,558,399 B1 | 1/2017 | Jeka et al. |
| 9,568,382 B1 | 2/2017 | Berme et al. |
| 9,622,686 B1 | 4/2017 | Berme et al. |
| 9,763,604 B1 | 9/2017 | Berme et al. |
| 9,770,203 B1 | 9/2017 | Berme et al. |
| 9,778,119 B2 | 10/2017 | Berme et al. |
| 9,814,430 B1 | 11/2017 | Berme et al. |
| 9,829,311 B1 | 11/2017 | Wilson et al. |
| 9,854,997 B1 | 1/2018 | Berme et al. |
| 9,916,011 B1 | 3/2018 | Berme et al. |
| 9,927,312 B1 | 3/2018 | Berme et al. |
| 10,010,248 B1 | 7/2018 | Shearer |
| 10,010,286 B1 | 7/2018 | Berme et al. |
| 10,085,676 B1 | 10/2018 | Berme et al. |
| 10,117,602 B1 | 11/2018 | Berme et al. |
| 10,126,186 B2 | 11/2018 | Berme et al. |
| 10,216,262 B1 | 2/2019 | Berme et al. |
| 10,231,662 B1 | 3/2019 | Berme et al. |
| 10,264,964 B1 | 4/2019 | Berme et al. |
| 10,331,324 B1 | 6/2019 | Wilson et al. |
| 10,342,473 B1 | 7/2019 | Berme et al. |
| 10,390,736 B1 | 8/2019 | Berme et al. |
| 10,413,230 B1 | 9/2019 | Berme et al. |
| 10,463,250 B1 | 11/2019 | Berme et al. |
| 10,527,508 B2 | 1/2020 | Berme et al. |
| 10,555,688 B1 | 2/2020 | Berme et al. |
| 10,646,153 B1 | 5/2020 | Berme et al. |
| 10,722,114 B1 | 7/2020 | Berme et al. |
| 10,736,545 B1 | 8/2020 | Berme et al. |
| 10,765,936 B2 | 9/2020 | Berme et al. |
| 10,803,990 B1 | 10/2020 | Wilson et al. |
| 10,853,970 B1 | 12/2020 | Akbas et al. |
| 10,856,796 B1 | 12/2020 | Berme et al. |
| 10,860,843 B1 | 12/2020 | Berme et al. |
| 10,945,599 B1 | 3/2021 | Berme et al. |
| 10,966,606 B1 | 4/2021 | Berme |
| 11,033,453 B1 | 6/2021 | Berme et al. |
| 11,052,288 B1 | 7/2021 | Berme et al. |
| 11,054,325 B2 | 7/2021 | Berme et al. |
| 11,074,711 B1 | 7/2021 | Akbas et al. |
| 11,097,154 B1 | 8/2021 | Berme et al. |
| 11,158,422 B1 | 10/2021 | Wilson et al. |
| 11,182,924 B1 | 11/2021 | Akbas et al. |
| 11,262,231 B1 | 3/2022 | Berme et al. |
| 11,262,258 B2 | 3/2022 | Berme et al. |
| 11,301,045 B1 | 4/2022 | Berme et al. |
| 11,311,209 B1 | 4/2022 | Berme et al. |
| 11,321,868 B1 | 5/2022 | Akbas et al. |
| 11,337,606 B1 | 5/2022 | Berme et al. |
| 11,348,279 B1 | 5/2022 | Akbas et al. |
| 11,458,362 B1 | 10/2022 | Berme et al. |
| 11,521,373 B1 | 12/2022 | Akbas et al. |
| 11,540,744 B1 | 1/2023 | Berme |
| 11,604,106 B2 | 3/2023 | Berme et al. |
| 11,631,193 B1 | 4/2023 | Akbas et al. |
| 11,688,139 B1 | 6/2023 | Karagoz et al. |
| 11,705,244 B1 | 7/2023 | Berme |
| 11,712,162 B1 | 8/2023 | Berme et al. |
| 11,790,536 B1 | 10/2023 | Berme et al. |
| 11,798,182 B1 | 10/2023 | Karagoz et al. |
| 11,816,258 B1 | 11/2023 | Berme et al. |
| 11,826,601 B1 | 11/2023 | Berme |
| 11,850,078 B1 | 12/2023 | Berme |
| 11,857,331 B1 | 1/2024 | Berme et al. |
| 11,865,407 B1 | 1/2024 | Berme et al. |
| 11,911,147 B1 | 2/2024 | Berme et al. |
| 2002/0057380 A1 | 5/2002 | Matey |
| 2002/0178008 A1 | 11/2002 | Reynar |
| 2003/0216656 A1 | 11/2003 | Berme et al. |
| 2004/0127337 A1 | 7/2004 | Nashner |
| 2004/0260427 A1 | 12/2004 | Wimsatt |
| 2006/0265249 A1 | 11/2006 | Follis et al. |
| 2008/0183981 A1 | 7/2008 | Tannai |
| 2008/0228110 A1 | 9/2008 | Berme |
| 2009/0062092 A1 | 3/2009 | Mortimer et al. |
| 2009/0251130 A1 | 10/2009 | Lund |
| 2011/0277562 A1 | 11/2011 | Berme |
| 2012/0123701 A1 | 5/2012 | Drueding et al. |
| 2012/0266648 A1 | 10/2012 | Berme et al. |
| 2012/0271565 A1 | 10/2012 | Berme et al. |
| 2013/0018282 A1 | 1/2013 | Mainini et al. |
| 2013/0171601 A1 | 7/2013 | Yuasa et al. |
| 2015/0096387 A1 | 4/2015 | Berme et al. |
| 2016/0245711 A1 | 8/2016 | Berme et al. |
| 2016/0334288 A1 | 11/2016 | Berme et al. |
| 2018/0024015 A1 | 1/2018 | Berme et al. |
| 2019/0078951 A1 | 3/2019 | Berme et al. |
| 2020/0139229 A1 | 5/2020 | Berme et al. |
| 2020/0408625 A1 | 12/2020 | Berme et al. |
| 2021/0333163 A1 | 10/2021 | Berme et al. |
| 2022/0178775 A1 | 6/2022 | Berme et al. |

OTHER PUBLICATIONS

Bertec Force Plates, Bertec Corporation, Version 1.0.0, last updated Mar. 2012.

Author: Todd Wilson, Bertec Workbook: Program Documentation, Version 1.0.0, Feb. 2010, pp. 47 Source: http://web.archive.org/web20110918144039/http://bertec.com/uploads/pdfs/manuals/Bertec%20Workbook.pdf.

First office action on the merits (Non-Final Rejection) in U.S. Appl. No. 13/726,065, mailed on Mar. 25, 2013.

Notice of Allowance in U.S. Appl. No. 13/726,065, mailed on Jul. 1, 2013.

First office action on the merits (Non-Final Rejection) in U.S. Appl. No. 14/042,332, mailed on Apr. 9, 2014.

Notice of Allowance in U.S. Appl. No. 14/042,332, mailed on Aug. 1, 2014.

First office action on the merits (Non-Final Rejection) in U.S. Appl. No. 14/556,656, mailed on Feb. 18, 2015.

Notice of Allowance in U.S. Appl. No. 14/556,656, mailed on Jul. 28, 2015.

First office action on the merits (Non-Final Rejection) in U.S. Appl. No. 14/953,505, mailed on Oct. 21, 2016.

Second office action on the merits (Final Rejection) in U.S. Appl. No. 14/953,505, mailed on Mar. 6, 2017.

Notice of Allowance in U.S. Appl. No. 14/953,505, mailed on Jul. 26, 2017.

Thelen et al., 2009, Foot force measurement by a force platform, BME 315 Biomechanics, 8 pages.

First office action on the merits (Non-Final Rejection) in U.S. Appl. No. 15/822,135, mailed on Nov. 13, 2018.

Notice of Allowance in U.S. Appl. No. 15/822,135, mailed on Feb. 6, 2019.

First office action on the merits (Non-Final Rejection) in U.S. Appl. No. 16/450,377, mailed on Nov. 19, 2019.

Notice of Allowance in U.S. Appl. No. 16/450,377, mailed on Jun. 15, 2020.

Lei, Ying, et al. "Algorithms for time synchronization of wireless structural monitoring sensors." Earthquake engineering & structural dynamics 34.6 (2005): 555-573.

Liu, Tao, et al. "A mobile force plate and three-dimensional motion analysis system for three-dimensional gait assessment." IEEE Sensors Journal 12.5 (2011): 1461-1467.

Waele, Stijn, and Piet MT Broersen. "Error measures for resampled irregular data." IEEE Transactions on Instrumentation and Measurement 49.2 (2000): 216-222.

First office action on the merits (Non-Final Rejection) in U.S. Appl. No. 17/068,181, mailed on Mar. 2, 2021.

First office action on the merits (Non-Final Rejection) in U.S. Appl. No. 17/509,838, mailed on Jul. 12, 2022.

Second office action on the merits (Final Rejection) in U.S. Appl. No. 17/509,838, mailed on Nov. 23, 2022.

Notice of Allowance in U.S. Appl. No. 17/509,838, mailed on Mar. 2, 2023.

(56) References Cited

OTHER PUBLICATIONS

Williams, A. Mark, and K. Anders Ericsson. "Perceptual-cognitive expertise in sport: Some considerations when applying the expert performance approach." Human movement science 24.3 (2005): 283-307.

Milner, Clare E., et al. "Biomechanical factors associated with tibial stress fracture in female runners." Medicine and science in sports and exercise 38.2 (2006): 323.

Muniz, A. M. S., et al. "Comparison among probabilistic neural network, support vector machine and logistic regression for evaluating the effect of subthalamic stimulation in Parkinson disease on ground reaction force during gait." Journal of biomechanics 43.4 (2010): 720-726.

* cited by examiner

FIG. 1

SECTION A-A

FORCE AND/OR MOTION MEASUREMENT SYSTEM THAT INCLUDES AT LEAST ONE KINEMATIC SENSOR DEVICE AND AT LEAST ONE DATA PROCESSING DEVICE CONFIGURED TO EXECUTE COMPUTER EXECUTABLE INSTRUCTIONS FOR DETERMINING A POSITION AND/OR MOVEMENT OF A PERSON BASED UPON OUTPUT DATA FROM THE AT LEAST ONE KINEMATIC SENSOR DEVICE

CROSS-REFERENCE TO RELATED APPLICATIONS

This is a continuation-in-part of U.S. Nonprovisional patent application Ser. No. 17/509,838, entitled "Force And/Or Motion Measurement System", filed on Oct. 25, 2021, the disclosure of which is hereby incorporated by reference as if set forth in its entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a force and/or motion measurement system. More particularly, the invention relates to a force and/or motion measurement system that includes a kinematic sensor device for detecting a position and/or movement of a body portion of a person.

2. Background

Measurement and testing systems are utilized in various fields to detect and analyze many different measurable quantities. For example, in biomedical applications, measurement and testing systems are used for gait analysis, assessing balance and mobility, evaluating sports performance, and assessing ergonomics. However, conventional measurement and testing systems have numerous limitations and drawbacks.

For example, conventional measurement and testing systems are typically complex systems located in a gait lab, which are difficult to incorporate in a natural environment outside of the gait lab. However, data collection in a natural environment outside the gait lab tends to produce results that are more illustrative of a person's natural gait.

Therefore, what is needed is a force and/or motion measurement system that includes a kinematic sensor device, which is suitable for data collection in a natural environment. Further, a need exists for a force and/or motion measurement system that includes a kinematic sensor device that is mounted in a floor of a room or in a force measurement assembly for easily and inconspicuously capturing the motion of a person.

BRIEF SUMMARY OF EMBODIMENTS OF THE INVENTION

Accordingly, the present invention is directed to a force and/or motion measurement system that substantially obviates one or more problems resulting from the limitations and deficiencies of the related art.

In accordance with one or more embodiments of the present invention, there is provided a force and/or motion measurement system that comprises at least one kinematic sensor device configured to detect a position and/or movement of a body portion of a person, the at least one kinematic sensor device being mounted in a floor of a room or in a force measurement assembly; and at least one data processing device operatively coupled to the at least one kinematic sensor device, the at least one data processing device including at least one hardware component storing computer executable instructions, and the at least one data processing device configured to execute the computer executable instructions. The computer executable instructions comprise instructions for determining a position and/or movement of the person based upon output data from the at least one kinematic sensor device.

In a further embodiment of the present invention, the at least one kinematic sensor device is selected from the group consisting of: (i) a sonar-based sensor, (ii) a sensor using wireless network technology, (iii) a LIDAR sensor, (iv) an ultrasonic sensor, (v) a camera, and (vi) combinations thereof.

In yet a further embodiment, the at least one kinematic sensor device is mounted in the floor of the room.

In still a further embodiment, the force and/or motion measurement system further comprises a force measurement assembly that includes a top component for receiving at least a portion of the body of the person; and at least one force transducer, the at least one force transducer configured to sense one or more measured quantities and output one or more signals that are representative of forces and/or moments being applied to the top component of the force measurement assembly by the person. In this further embodiment, the force measurement assembly is operatively coupled to the at least one data processing device, and the computer executable instructions further comprise instructions for: (i) receiving the one or more signals that are representative of the forces and/or moments being applied to the top component of the force measurement assembly by the person, and (ii) converting the one or more signals into output forces and/or moments. Also, in this further embodiment, the at least one kinematic sensor device is mounted in the force measurement assembly.

In yet a further embodiment, the at least one kinematic sensor device is disposed below or generally flush with an upper surface of the top component of the force measurement assembly.

In still a further embodiment, the at least one kinematic sensor device comprises one or more additional kinematic sensor devices mounted in the floor of the room.

In yet a further embodiment, the at least one kinematic sensor device is configured to detect a lower body motion of the person; and the computer executable instructions further comprise instructions for predicting one or more ground reaction forces of the person using the output data from the at least one kinematic sensor device for the lower body motion of the person.

In still a further embodiment, the computer executable instructions further comprise instructions for predicting the one or more ground reaction forces of the person using a trained neural network.

In accordance with one or more other embodiments of the present invention, there is provided a force and/or motion measurement system that comprises at least one kinematic sensor device configured to detect a position and/or movement of a body portion of a person, the at least one kinematic sensor device not requiring a line of sight to the person to detect the position and/or movement of the body portion of the person; and at least one data processing device operatively coupled to the at least one kinematic sensor device, the at least one data processing device including at least one hardware component storing computer executable instructions, and the at least one data processing device configured to execute the computer executable instructions. The computer executable instructions comprise instructions for determining a position and/or movement of the person based upon output data from the at least one kinematic sensor device.

In a further embodiment of the present invention, the at least one kinematic sensor device is selected from the group consisting of: (i) a sonar-based sensor, (ii) a sensor using wireless network technology, and (iii) combinations thereof.

In yet a further embodiment, the at least one kinematic sensor device is mounted in a floor of a room.

In still a further embodiment, the force and/or motion measurement system further comprises a force measurement assembly that includes a top component for receiving at least a portion of the body of the person; and at least one force transducer, the at least one force transducer configured to sense one or more measured quantities and output one or more signals that are representative of forces and/or moments being applied to the top component of the force measurement assembly by the person. In this further embodiment, the force measurement assembly is operatively coupled to the at least one data processing device, and the computer executable instructions further comprise instructions for: (i) receiving the one or more signals that are representative of the forces and/or moments being applied to the top component of the force measurement assembly by the person, and (ii) converting the one or more signals into output forces and/or moments. Also, in this further embodiment, the at least one kinematic sensor device is mounted in the force measurement assembly.

In yet a further embodiment, the at least one kinematic sensor device is disposed below or generally flush with an upper surface of the top component of the force measurement assembly.

In still a further embodiment, the at least one kinematic sensor device comprises one or more additional kinematic sensor devices mounted in the floor of the room.

In yet a further embodiment, the at least one kinematic sensor device is configured to detect a lower body motion of the person; and the computer executable instructions further comprise instructions for predicting one or more ground reaction forces of the person using the output data from the at least one kinematic sensor device for the lower body motion of the person.

In still a further embodiment, the computer executable instructions further comprise instructions for predicting the one or more ground reaction forces of the person using a trained neural network.

In accordance with yet one or more other embodiments of the present invention, there is provided a force and/or motion measurement system that comprises a force measurement assembly that includes a top component for receiving at least a portion of the body of the person; and at least one force transducer, the at least one force transducer configured to sense one or more measured quantities and output one or more signals that are representative of forces and/or moments being applied to the top component of the force measurement assembly by the person; at least one kinematic sensor device configured to detect a position and/or movement of a body portion of a person, the at least one kinematic sensor device being mounted in the force measurement assembly; and at least one data processing device operatively coupled to the at least one kinematic sensor device and the force measurement assembly, the at least one data processing device including at least one hardware component storing computer executable instructions, and the at least one data processing device configured to execute the computer executable instructions. The computer executable instructions comprise instructions for: (i) determining a position and/or movement of the person based upon output data from the at least one kinematic sensor device; (ii) receiving the one or more signals that are representative of the forces and/or moments being applied to the top component of the force measurement assembly by the person; and (iii) converting the one or more signals into output forces and/or moments.

In a further embodiment of the present invention, the at least one kinematic sensor device is selected from the group consisting of: (i) a sonar-based sensor, (ii) a sensor using wireless network technology, (iii) a LIDAR sensor, (iv) an ultrasonic sensor, (v) a camera, and (vi) combinations thereof.

In yet a further embodiment, the at least one kinematic sensor device is configured to detect a lower body motion of the person; and the computer executable instructions further comprise instructions for predicting one or more ground reaction forces of the person using the output data from the at least one kinematic sensor device for the lower body motion of the person.

In still a further embodiment, the computer executable instructions further comprise instructions for predicting the one or more ground reaction forces of the person using a trained neural network.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

The present invention is described herein, in an exemplary manner, with reference to hardware components and computer system architecture that illustrate exemplary processes carried out by the computer system. In a preferred embodiment, the functionality of the system can be implemented by computer system instructions. These computer program instructions may be loaded directly onto an internal data storage device of a computing device (e.g., a hard drive of a computer). Alternatively, these computer program instructions could be stored on a portable computer-readable medium (e.g., a flash drive, a floppy disk, a compact disk, etc.), and then subsequently loaded onto a computing device such that the instructions can be executed thereby. In other embodiments, these computer program instructions could be embodied in the hardware of the computing device, rather than in the software thereof. It is also possible for the computer program instructions to be embodied in a combination of both the hardware and the software. Also, in the disclosure, when a reference is made to a computing device that is "configured to", "arranged to" and/or "configured and arranged to" perform a specific function (e.g., a data acquisition/data processing device configured and arranged to perform a specific function), it is to be understood that, in one or more embodiments of the invention, this means that the computing device is specially programmed to carry out the particular function (e.g., the data acquisition/data processing device being specially programmed to perform a specific function).

This description describes in general form the computer program(s) required to carry out the various features of the invention. Any competent programmer in the field of information technology could develop a functioning system using the description set forth herein.

For the sake of brevity, conventional computer system components, conventional data networking, and conventional software coding will not be described in detail herein. Also, it is to be understood that the connecting lines shown in the figure(s) included herein are intended to represent functional relationships and/or operational couplings between the various components. In addition to that which is explicitly depicted, it is to be understood that many alternative or additional functional relationships and/or physical connections may be incorporated in a practical application of the system.

Figure 1:
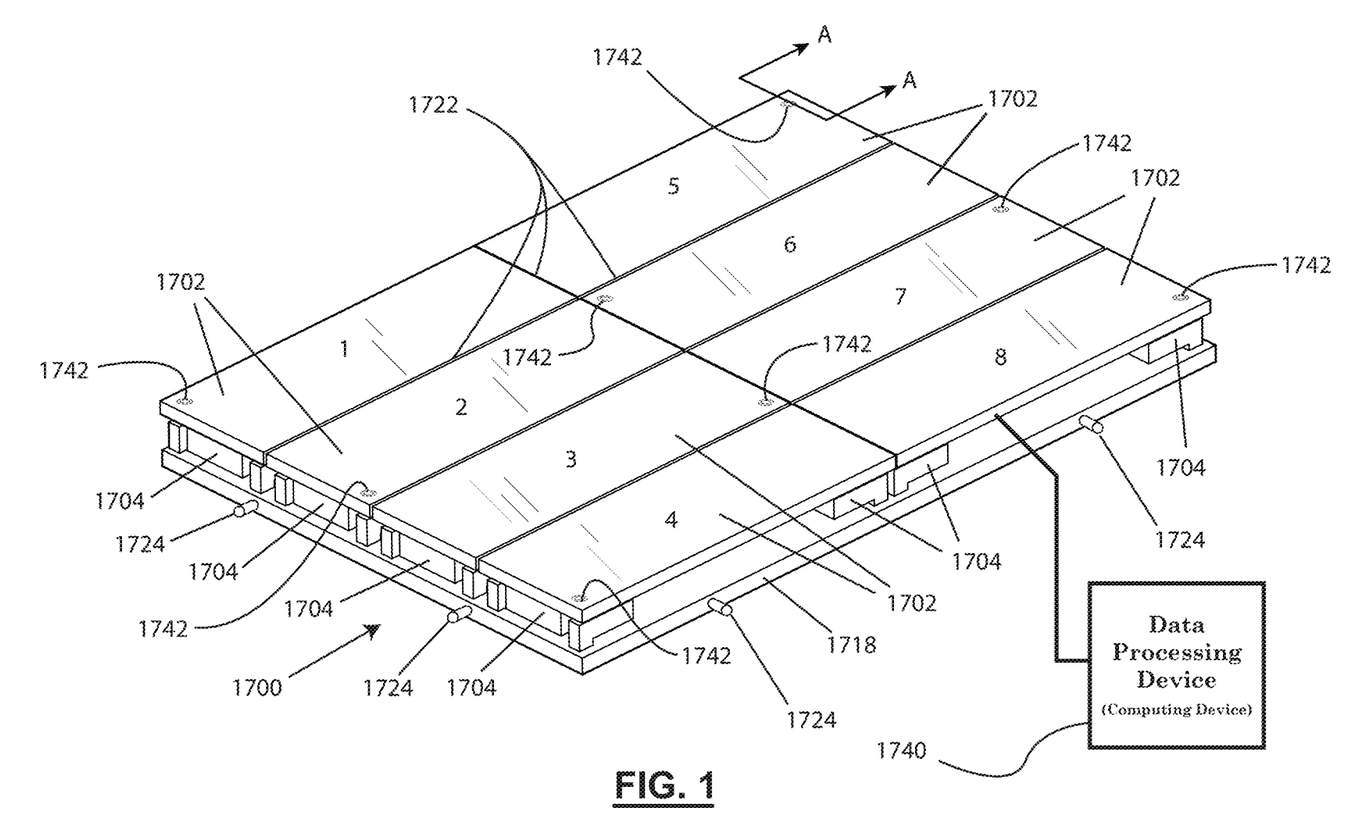
FIG. 1 is a perspective view of a force plate module of a force measurement system with a motion capture camera provided in each force plate of the force plate module, according to an embodiment of the invention.
Figure 2:
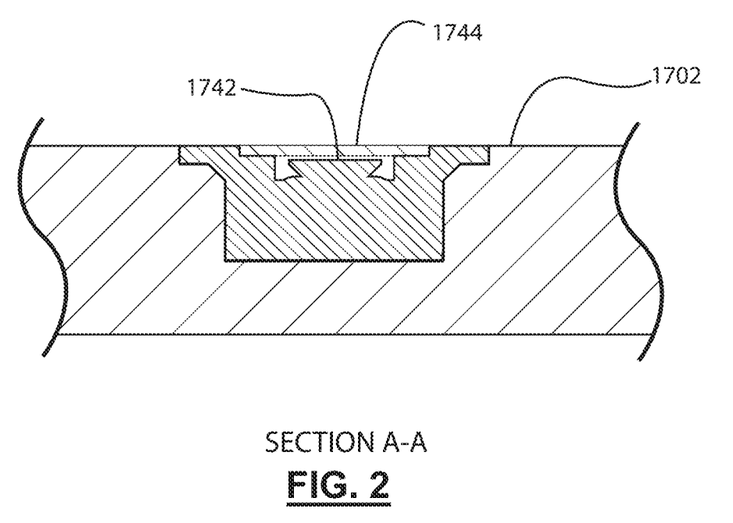
FIG. 2 is a sectional view cut through one of the force plates of the force plate module of FIG. 1, wherein the section is generally cut along the cutting-plane line A-A in FIG. 1.
Figure 3:
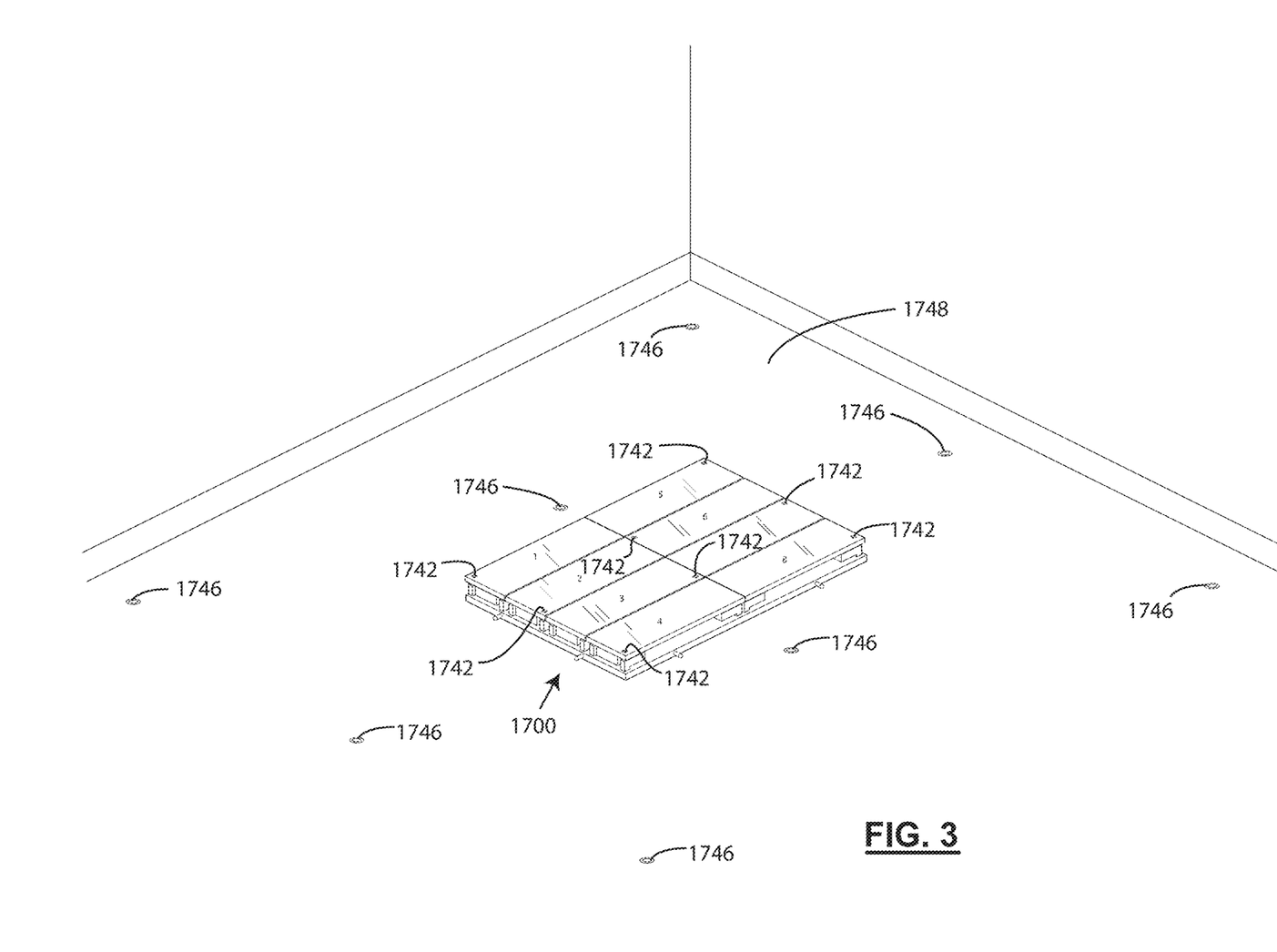
FIG. 3 is a perspective view of a room with a floor having a plurality of motion capture cameras disposed therein, according to a variation of the embodiment of FIG. 1.

A first illustrative embodiment of a force and/or motion measurement system is depicted in FIGS. 1-3. In this illustrative embodiment, the force and/or motion measurement system includes a plurality of force measurement assemblies (e.g., the force plate assemblies described in further detail below), a motion capture subsystem (see FIGS. 1 and 3), and a data processing device (e.g., the computing device 1740 described in further detail below) operatively coupled to the motion capture subsystem and each of the force transducers of each of the force plate assemblies. In this illustrative embodiment, the motion capture subsystem is markerless-type motion capture system that comprises a plurality of cameras 1742 configured to detect a motion of a person (refer to FIG. 1). As shown in FIG. 1, each of the plurality of force plate cameras 1742 is mounted in a top plate component 1702 of the force plate assembly. Also, in this illustrative embodiment, the data processing device (e.g., the computing device 1740 described above) is configured to determine a position and/or movement of one or more limbs of the person based upon output data from the plurality of cameras 1742 of the motion capture subsystem.

Turning to FIG. 3, in the illustrative embodiment, another plurality of cameras 1746 may be mounted in a floor 1748 of a room (e.g., in the area surrounding the force measurement assemblies). Like the force plate cameras 1742 described above, each of the plurality of floor-mounted cameras 1746 is operatively coupled to the data processing device (e.g., the computing device 1740). For example, in the illustrative embodiment, each of the motion capture cameras 1742, 1746 may be wirelessly connected to the data processing device 1740. Similar to the cameras 1742, the plurality of floor-mounted cameras 1746 are configured to detect a motion of a person (refer to FIG. 3). Also, in the illustrative embodiment, the data processing device 1740 is configured to determine a position and/or movement of one or more limbs of the person based upon output data from the plurality of floor-mounted cameras 1746 of the motion capture subsystem.

With combined reference to FIGS. 1 and 2, it can be seen that, in the illustrative embodiment, a top surface of each of the force plate cameras 1742 is disposed generally flush with an upper surface of the top component 1702 of the force measurement assembly. More specifically, as shown in FIG. 2, it can be seen that each force plate camera 1742 may be provided with a transparent lens plate 1744 (e.g., a glass or plastic plate 1744) that is disposed generally flush with an upper surface of the top component 1702 of the force measurement assembly. Advantageously, the transparent lens plate 1744 protects the lens of the force plate camera 1742 from damage which could result from a person disposed on the force measurement assembly stepping on the camera 1742.

In the illustrative embodiment, as shown in FIG. 3, it can be seen that a top surface of each of the floor-mounted cameras 1746 is disposed generally flush with an upper surface of the floor 1748 of the room. Similar to the force plate cameras 1742, each floor-mounted camera 1746 may be provided with a transparent lens plate that is disposed generally flush with an upper surface of the floor 1748. Advantageously, the transparent lens plate protects the lens of the floor-mounted camera 1746 from damage which could result from a person disposed on the floor 1748 stepping on the camera 1746. In the illustrative embodiment, each floor-mounted camera 1746 may be inconspicuously mounted in the floor 1748 of the room so that the motion of the person is able to be undetectably captured in a natural environment of the person (i.e., the person will not be aware of the cameras 1746 so that he or she will not alter his or her gait behavior as a result of being recorded by the motion capture subsystem). As such, the gait of the person is able to be assessed using the motion capture subsystem without the person being aware of the assessment. Also, the floor mounting and force plate mounting of the cameras 1742, 1746 advantageously obviates the need for supporting the cameras from an overhead support structure.

In the illustrative embodiment, the floor-mounted cameras 1746 are configured to detect a lower body motion of the person (refer to FIG. 3); and the data processing device 1740 is further configured to predict one or more ground reaction forces of the person using the output data from the floor-mounted cameras 1746 of the motion capture subsystem for the lower body motion of the person (i.e., the one or more ground reaction forces of the person can be estimated when the person is walking on the floor 1748 so that the person does not have to be disposed on the array of force measurement assemblies for the ground reaction forces to be estimated). That way, ground reaction forces can advantageously be estimated when the person is walking around in a normal setting, such as in the room of a building or in a room of the person's home. In the illustrative embodiment, the data processing device 1740 is configured to predict the one or more ground reaction forces of the person using a trained neural network to analyze the output data from the floor-mounted cameras 1746 of the motion capture subsystem. For example, the neural network is trained initially using force plate data, and then the trained neural network is able to use the output data from the floor-mounted cameras 1746 to estimate the one or more ground reaction forces of the person when he or she is walking around on the floor 1748. In the illustrative embodiment, once the positional data is obtained using the motion capture subsystem of FIGS. 1 and 3, the data processing device 1740 utilizes inverse dynamics in order to estimate the ground reaction forces from the kinematic data obtained from the cameras 1742, 1746.

Now, turning to FIG. 1, it can be seen that, in the illustrative embodiment, the force plate module 1700 includes a plurality of force plate assemblies in the form of force plates that are disposed adjacent to one another, and each being separated by a narrow gap 1722 (see FIG. 1). As depicted in FIG. 1, the plurality of force plate assemblies of the force plate module 1700 are supported on a common base component 1718, which is in the form of a continuous base plate that extends underneath all of the module force plate assemblies in the illustrated embodiment. Also, in the illustrated embodiment, each of the force plate assemblies includes a top plate component 1702 having an upper surface, the upper surface of each top plate component 1702 forming a force measurement surface for receiving at least one portion of a body of a subject (e.g., a foot/leg of a subject). In addition, each of the illustrated module force plate assemblies is provided with a plurality of force transducers 1704 (e.g., a pair of transducer beams) disposed underneath, and supporting the top plate component 1702. The force transducers of the force plate assemblies are configured to sense one or more measured quantities and output one or more signals that are representative of the one or more measured quantities (i.e., force and/or moments). In one or more embodiments, a subject stands in an upright position on the force plate module 1700 in FIG. 1, and each foot of the subject is placed on one or more top surfaces of the force plates in the force plate module 1700. In FIG. 1, each force plate assembly of the force plate module 1700 is identified by a corresponding identification number (i.e., force plate no. 1, 2, 3, 4, 5, 6, 7, and 8).

With reference primarily to FIG. 1 of the illustrative embodiment, the force transducers 1704 of each force plate assembly of the force plate module 1700 will be described in detail. As shown in the perspective view of FIG. 1, each of the pair of force transducers 1704 is disposed proximate to one of the opposite longitudinal ends of the top plate component 1702 of each force plate assembly. Each of the force transducers 1704 generally comprises a central rectangular body portion with an upper standoff portion, first and second L-shaped transducer beam portions that wrap around a portion of the outer periphery of the rectangular body portion, and a beam connector portion that connects each of the first and second L-shaped transducer beam portions to a common side of the rectangular body portion. Each of the first and second L-shaped transducer beam portions is oppositely disposed with respect to one another, and, except for the connector portion, each of the first and second L-shaped transducer beam portions is spaced apart from the outer side surfaces of the rectangular body portion by a continuous narrow gap. Each of the L-shaped transducer beam portions comprises two transducer beam sections perpendicularly disposed relative to one another, namely a proximal beam section connected to the connector portion and a distal beam section with a lower standoff portion. The upper standoff portion (i.e., the raised top surface) of rectangular body portion elevates the top plate component 1702 above the top surfaces of the L-shaped transducer beam portions so as to create a gap between the top surfaces of the L-shaped transducer beam portions and the bottom surface of the top plate component 1702, whereas the lower standoff portions of the distal beam sections elevate the bottom surfaces of the L-shaped transducer beam portions above the top surface of the base plate component 1718 so as to create a gap between the top surface of the base plate component 1718 and the bottom surfaces of the L-shaped transducer beam portions. As such, in the illustrative embodiment, the structural components 1702, 1718 to which the force transducers 1704 are mounted are connected only to the upper standoff portion of the rectangular body portion and the lower standoff portions of the distal beam sections so as to ensure that the total load applied to the force transducers 1704 is transmitted through the transducer beam portions. The compact structural configuration of the force transducers 1704 enables the force transducers 1704 to be effectively utilized in the force plate module 1700, which comprises the plurality of small force plate assemblies (i.e., force plate nos. 1, 2, 3, 4, 5, 6, 7, and 8).

In the illustrative embodiment, each of the L-shaped transducer beam portions may comprises a plurality of strain gages for detecting the deformation in the beam sections of the L-shaped transducer beam portions resulting from the applied load. For example, in the illustrative embodiment, the force transducers 1704 of each force plate assembly of the force plate module 1700 may be sensitive to the vertical force ($F_z$) and the moments in the x and y directions ($M_x$, $M_y$). Alternatively, the force transducers 1704 of each force plate assembly of the force plate module 1700 may be sensitive to all six (6) force and moment components ($F_x$, $F_y$, $F_z$, $M_x$, $M_y$, $M_z$).

In the illustrative embodiment, each of the force transducers 1704 includes a plurality of strain gages wired in one or more Wheatstone bridge configurations, wherein the electrical resistance of each strain gage is altered when the associated portion of the force transducer undergoes deformation resulting from the load (i.e., forces and/or moments) acting on the top plate component 1702. For each plurality of strain gages disposed on the force transducers 1704, the change in the electrical resistance of the strain gages brings about a consequential change in the output voltage of the Wheatstone bridge (i.e., a quantity representative of the load being applied to the measurement surface). In the illustrative embodiment, each force transducer 1704 outputs a plurality of analog output voltages (signals).

In the illustrative embodiment, the data acquisition and processing device 1740 (i.e., computing device 1740) may comprise a microprocessor for processing data from the force plate assemblies of the force plate module 1700, memory (e.g., random access memory or RAM) for storing data during the processing thereof, and data storage device(s), such as one or more hard drives, compact disk drives, floppy disk drives, flash drives, or any combination thereof. Also, the data acquisition and processing device 1740 may comprise user input devices in the form of a keyboard, mouse, and touchpad or touchscreen.

In the illustrative embodiment, each of the force plate assemblies may comprise a dedicated digitizer and signal conditioner that is electrically coupled to each of the force transducers 1704 of the respective force plate assembly by electrical transducer wiring. Each digitizer and signal conditioner converts the analog voltage signals from the transducers 1704 of its respective force plate assembly into digital voltage signals, and may also perform other functions on the signals as well, such as amplification, filtering, etc. In the illustrative embodiment, it can be seen that each force plate digitizer and signal conditioner is electrically coupled to an electrical interface of the force plate module 1700 by electrical wiring (e.g., by Universal Serial Bus (USB) cables). The electrical interface of the force plate module 1700 may comprise one or more electrical ports for receiving one or more respective wiring plug connectors of electrical cables that transfer data and/or power to, and from, the force plate module 1700. For example, as diagrammatically shown in FIG. 1, the electrical interface of the force plate module 1700 is electrically coupled to the data acquisition and processing device 1740 by an electrical cable so that the signals from the force transducers 1704 of the force plate assemblies may be converted into output loads (i.e., into forces and/or moments) by multiplying the voltage signals by a calibration matrix. Alternatively, the force plate digitizer and signal conditioner may convert the signals from the force transducers 1704 of the force plate assemblies into output loads (i.e., into forces and/or moments) by multiplying the voltage signals by a calibration matrix.

In one or more embodiments, the electrical interface of the force plate module 1700 may comprise a plurality of electrical ports, which include a Universal Serial Bus (USB) port, an Ethernet port, a power over Ethernet (POE) port, and an additional power input port.

Figure 4:
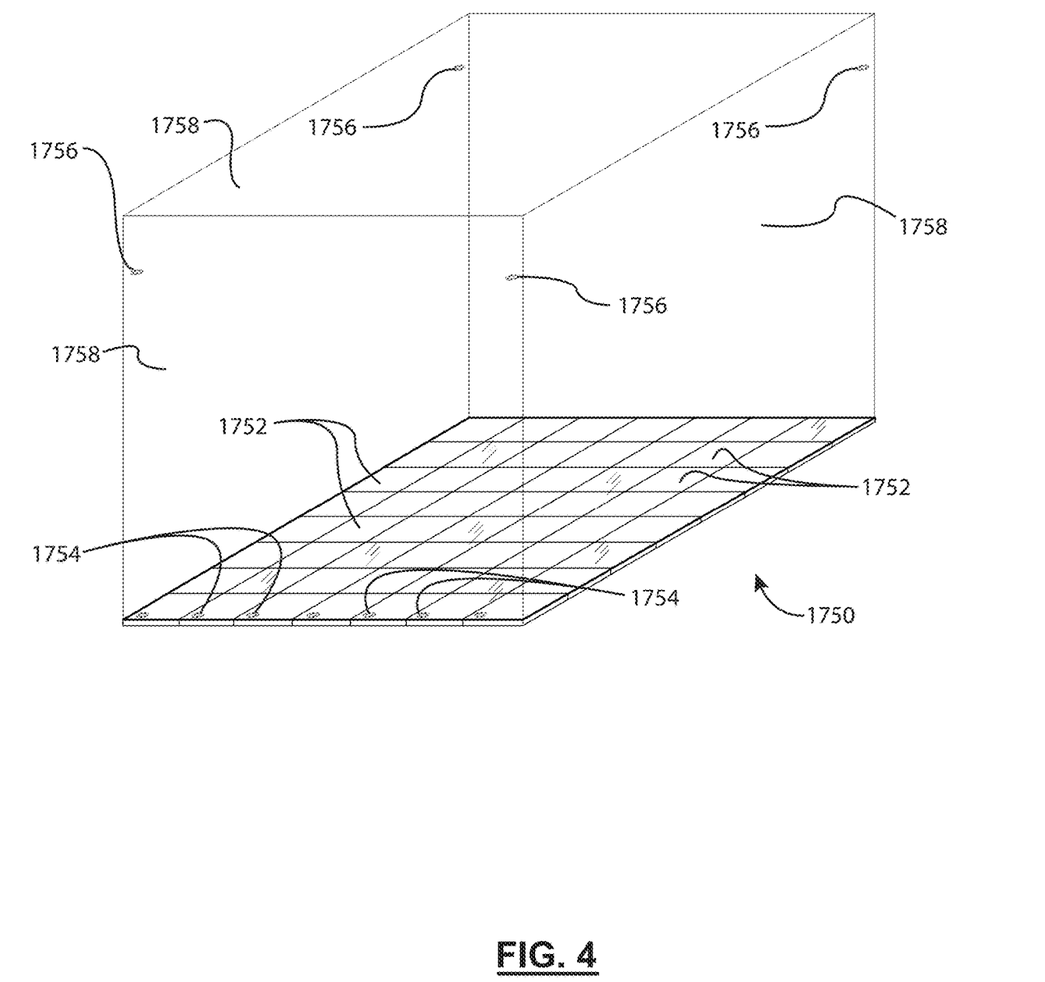
FIG. 4 is a perspective view of a room with a floor having a plurality of force plate modules and a plurality of kinematic sensor devices disposed in at least some of the force plate modules and in other areas of the room, according to another embodiment of the invention.

A second illustrative embodiment a force and/or motion measurement system is depicted in FIG. 4. In this illustrative embodiment, the force and/or motion measurement system includes a plurality of force measurement assemblies 1752 (e.g., the force plate assemblies described in detail above) disposed on a floor of a room 1750, a plurality of kinematic sensor devices 1754, 1756 configured to detect a position and/or movement of a body portion of a person; and a data processing device (e.g., the computing device 1740 described in detail above) operatively coupled to the plurality of kinematic sensor devices 1754, 1756 and each of the force transducers of each of the force plate assemblies. In this illustrative embodiment, a first subset of the plurality of kinematic sensor devices 1754 may be mounted in the force measurement assemblies 1754 or in the floor of the room 1750, while a second subset of the plurality of kinematic sensor devices 1756 may be mounted on the walls 1758 of the room. In the illustrative embodiment, each of the plurality of kinematic sensor devices 1754, 1756 may be wirelessly connected to the data processing device 1740. Also, in this illustrative embodiment, the data processing device (e.g., the computing device 1740 described above) is configured to determine a position and/or movement of the person based upon output data from the plurality of kinematic sensor devices 1754, 1756.

In the illustrative embodiment, the kinematic sensor devices 1754, 1756 may be inconspicuously mounted in the force measurement assemblies 1752 and the wall 1758 of the room 1750 so that the motion of the person is able to be undetectably captured in a natural environment of the person (i.e., the person will not be aware of the kinematic sensor devices 1754, 1756 so that he or she will not alter his or her gait behavior as a result of being recorded by the kinematic sensor devices 1754, 1756). As such, the gait of the person is able to be assessed using the kinematic sensor devices 1754, 1756 without the person being aware of the assessment. Also, the force plate mounting and floor mounting of the kinematic sensor devices 1754 advantageously obviates the need for supporting the kinematic sensor devices from any structures above the person.

In the illustrative embodiment, the kinematic sensor devices 1754, 1756 are selected from the group consisting of: (i) sonar-based sensors, (ii) sensors using wireless network technology (e.g., Wi-Fi sensors), (iii) light detection and ranging (LIDAR) sensors, (iv) ultrasonic sensors, (v) cameras, and (vi) combinations thereof. In one or more embodiments, all or some of the force measurement assemblies 1752 may be provided with same type or different types of kinematic sensor devices. In the illustrative embodiment of FIG. 4, the kinematic sensor devices 1754 are disposed below or generally flush with the upper surfaces of the top components of the force measurement assemblies 1752.

In one or more embodiments, the type of kinematic sensor devices 1754, 1756 that are used do not require a line of sight to the person to detect the position and/or movement of the body portion of the person. For example, in these one or more embodiments, the kinematic sensor devices 1754, 1756 are selected from the group consisting of: (i) sonar-based sensors, (ii) sensors using wireless network technology (e.g., Wi-Fi sensors), and (iii) combinations thereof. In one or more embodiments, because the kinematic sensor devices 1754, 1756 do not require a line of sight, these sensor devices 1754, 1756 could be better protected from wear and damage over time, particularly when the sensor devices 1754, 1756 are mounted in the floor or in force plates forming the floor surface. In this application, it would be expected that surface-mounted sensors would be walked on and worn, thereby putting image/sensor quality at risk. Although, if kinematic sensor devices 1754, 1756 not requiring a line of sight were used, these sensor devices could be recessed mounted in the floor so that they would be much less susceptible to damage.

In one or more other embodiments, the kinematic sensor devices 1754, 1756 comprise a combination of light detection and ranging (LIDAR) sensors and video cameras. In these one or more other embodiments, the video cameras may be configured to sense a flat image (brightness, color) without depth information, while the LIDAR sensors (e.g., LIDAR cameras) provide, for each pixel, the distance information only. In these one or more other embodiments, the distance information provided by the LIDAR cameras is in a form of intensity of reflection versus depth for every pixel. Thus, the information provided by the LIDAR cameras is not just one distance per pixel, but a series of brightness (of reflected light) measurements taken along the depth of the field, in some depth increments. Because LIDAR sees more than just the primary reflection, it is suited for tracking objects behind mostly transparent obstacles. For example, there may be a transparent plastic stepping block placed on top of one of the force measurement assemblies 1752. The LIDAR sensor(s) will sense through that block. As another example, the LIDAR sensor(s) will sense through transparent stairs and other such accessories. The LIDAR sensor(s) can also sense through transparent tools, so if people interact within the field of view, the tools can be tracked accurately by placing tiny retroreflectors on them, while still allowing the pose of the subject to be captured. Video and LIDAR cameras are both characterized by the number of pixels in their images. Due to the principle of reciprocity, a LIDAR sensor can have one illuminator and multiple sensor pixels, or multiple illuminators (individually controllable) but just one sensor pixel. Both such LIDAR devices can have the same resolution expressed in number of pixels. In these one or more other embodiments, each pixel can obtained by a narrow illumination beam and wide angle sensor, or a wide angle illumination beam and narrow angle sensor.

In the illustrative embodiment, the kinematic sensor devices 1754 mounted in the force measurement assemblies 1752 are configured to detect a lower body motion of the person (refer to FIG. 4); and the data processing device 1740 is further configured to predict one or more ground reaction forces of the person using the output data from the kinematic sensor devices 1754 for the lower body motion of the person. That way, ground reaction forces can advantageously be estimated when the person is walking around in a normal setting, such as in the room of a building or in a room of the person's home. In the illustrative embodiment, the data processing device 1740 is configured to predict the one or more ground reaction forces of the person using a trained neural network to analyze the output data from the kinematic sensor devices 1754. For example, the neural network is trained initially using force plate data, and then the trained neural network is able to use the output data from just the kinematic sensor devices 1754 to estimate the one or more ground reaction forces of the person when he or she is walking around on the floor on the room 1750. In the illustrative embodiment, once the positional data is obtained using the kinematic sensor devices 1754 of FIG. 4, the data processing device 1740 utilizes inverse dynamics in order to estimate the ground reaction forces from the kinematic data obtained from the kinematic sensor devices 1754.

In one or more embodiments, the entire floor of the room (e.g., the room 1750 in FIG. 4) comprises an array of force plate assemblies 1752 that are also able to sense the position of the body segments of one or more persons using kinematic sensor devices 1754 disposed in the force plate assemblies 1752. In these one or more embodiments, the force plate assemblies 1752 with the kinematic sensor devices 1754 disposed therein form an array of devices 1754 so that the movement analysis of the one or more persons is able to be performed from the ground up, without requiring installation of kinematic sensor devices on the walls, etc. of the room.

It is readily apparent that the embodiments of the force and/or motion measurement system described above offer numerous advantages and benefits. For example, in one or more embodiments, the aforedescribed force and/or motion measurement system is suitable for data collection in a natural environment. In addition, in one or more embodiments, the force and/or motion measurement system may be used for easily and inconspicuously capturing the motion of a person.

Although the invention has been shown and described with respect to a certain embodiment or embodiments, it is apparent that this invention can be embodied in many different forms and that many other modifications and variations are possible without departing from the spirit and scope of this invention. Moreover, while reference is made throughout this disclosure to, for example, "an illustrative embodiment", "one embodiment" or a "further embodiment", it is to be understood that some or all aspects of these various embodiments may be combined with one another as part of an overall embodiment of the invention. Also, the compound conjunction "and/or" is used throughout this disclosure to mean one or the other, or both.

In addition, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A force and/or motion measurement system, comprising:
    at least one kinematic sensor device configured to detect a position and/or movement of a body portion of a person, the at least one kinematic sensor device being mounted in or on a bounding surface of a room or in a force measurement assembly; and
    at least one data processing device operatively coupled to the at least one kinematic sensor device, the at least one data processing device including at least one hardware component storing computer executable instructions, and the at least one data processing device configured to execute the computer executable instructions, the computer executable instructions comprising instructions for:
        determining a position and/or movement of the person based upon output data from the at least one kinematic sensor device; and
    wherein the at least one kinematic sensor device is selected from the group consisting of: (i) a sonar-based sensor, (ii) a sensor using wireless network technology, (iii) a LIDAR sensor, (iv) an ultrasonic sensor, and (v) combinations thereof.

2. The force and/or motion measurement system according to claim 1, wherein the bounding surface in or on which the at least one kinematic sensor device is mounted comprises a floor of the room.

3. The force and/or motion measurement system according to claim 1, wherein the force and/or motion measurement system comprises the force measurement assembly, and the force measurement assembly comprises:
    a top component for receiving at least a portion of the body of the person; and
    at least one force transducer, the at least one force transducer configured to sense one or more measured quantities and output one or more signals that are representative of forces and/or moments being applied to the top component of the force measurement assembly by the person;
    wherein the force measurement assembly is operatively coupled to the at least one data processing device, and the computer executable instructions further comprising instructions for:
    receiving the one or more signals that are representative of the forces and/or moments being applied to the top component of the force measurement assembly by the person, and
    converting the one or more signals into output forces and/or moments; and wherein the at least one kinematic sensor device is mounted in the force measurement assembly.

4. The force and/or motion measurement system according to claim 3, wherein the at least one kinematic sensor device is disposed below or generally flush with an upper surface of the top component of the force measurement assembly.

5. The force and/or motion measurement system according to claim 3, wherein the at least one kinematic sensor device comprises one or more additional kinematic sensor devices mounted in or on the bounding surface of the room.

6. The force and/or motion measurement system according to claim 1, wherein the at least one kinematic sensor device is configured to detect a lower body motion of the person; and
wherein the computer executable instructions further comprise instructions for:
predicting one or more ground reaction forces of the person using the output data from the at least one kinematic sensor device for the lower body motion of the person.

7. The force and/or motion measurement system according to claim 6, wherein the computer executable instructions further comprise instructions for:
predicting the one or more ground reaction forces of the person using a trained neural network.

8. A force and/or motion measurement system, comprising:
at least one kinematic sensor device configured to detect a position and/or movement of a body portion of a person, the at least one kinematic sensor device being mounted in or on a bounding surface of a room; and
at least one data processing device operatively coupled to the at least one kinematic sensor device, the at least one data processing device including at least one hardware component storing computer executable instructions, and the at least one data processing device configured to execute the computer executable instructions, the computer executable instructions comprising instructions for:
determining a position and/or movement of the person based upon output data from the at least one kinematic sensor device; and
wherein the at least one kinematic sensor device is selected from the group consisting of: (i) a sonar-based sensor, (ii) a sensor using wireless network technology, (iii) a LIDAR sensor, (iv) an ultrasonic sensor, and (v) combinations thereof.

9. The force and/or motion measurement system according to claim 8, wherein the force and/or motion measurement system further comprises a force measurement assembly, and the force measurement assembly comprises:
a top component for receiving at least a portion of the body of the person; and
at least one force transducer, the at least one force transducer configured to sense one or more measured quantities and output one or more signals that are representative of forces and/or moments being applied to the top component of the force measurement assembly by the person;
wherein the force measurement assembly is operatively coupled to the at least one data processing device, and the computer executable instructions further comprising instructions for:
receiving the one or more signals that are representative of the forces and/or moments being applied to the top component of the force measurement assembly by the person, and
converting the one or more signals into output forces and/or moments; and
wherein the at least one kinematic sensor device comprises one or more additional kinematic sensor devices mounted in the force measurement assembly.

10. The force and/or motion measurement system according to claim 9, wherein the one or more additional kinematic sensor devices are disposed below or generally flush with an upper surface of the top component of the force measurement assembly.

11. The force and/or motion measurement system according to claim 8, wherein the at least one kinematic sensor device is configured to detect a lower body motion of the person; and
wherein the computer executable instructions further comprise instructions for:
predicting one or more ground reaction forces of the person using the output data from the at least one kinematic sensor device for the lower body motion of the person.

12. The force and/or motion measurement system according to claim 11, wherein the computer executable instructions further comprise instructions for:
predicting the one or more ground reaction forces of the person using a trained neural network.

13. A force and/or motion measurement system, comprising:
a force measurement assembly including:
a top component for receiving at least a portion of the body of a person; and
at least one force transducer, the at least one force transducer configured to sense one or more measured quantities and output one or more signals that are representative of forces and/or moments being applied to the top component of the force measurement assembly by the person;
at least one kinematic sensor device configured to detect a position and/or movement of a body portion of the person, the at least one kinematic sensor device being mounted in the force measurement assembly; and
at least one data processing device operatively coupled to the at least one kinematic sensor device and the force measurement assembly, the at least one data processing device including at least one hardware component storing computer executable instructions, and the at least one data processing device configured to execute the computer executable instructions, the computer executable instructions comprising instructions for:
determining a position and/or movement of the person based upon output data from the at least one kinematic sensor device;
receiving the one or more signals that are representative of the forces and/or moments being applied to the top component of the force measurement assembly by the person; and
converting the one or more signals into output forces and/or moments.

14. The force and/or motion measurement system according to claim 13, wherein the at least one kinematic sensor device is selected from the group consisting of: (i) a sonar-based sensor, (ii) a sensor using wireless network technology, (iii) a LIDAR sensor, (iv) an ultrasonic sensor, (v) a camera, and (vi) combinations thereof.

15. The force and/or motion measurement system according to claim 13, wherein the at least one kinematic sensor device is configured to detect a lower body motion of the person; and
- wherein the computer executable instructions further comprise instructions for:
- predicting one or more ground reaction forces of the person using the output data from the at least one kinematic sensor device for the lower body motion of the person.

16. The force and/or motion measurement system according to claim 15, wherein the computer executable instructions further comprise instructions for:
- predicting the one or more ground reaction forces of the person using a trained neural network.

* * * * *